United States Patent
Lee

(10) Patent No.: US 11,426,508 B2
(45) Date of Patent: Aug. 30, 2022

(54) SNIVEL SUCTION APPARATUS

(71) Applicant: TAI-SHINY TECHNOLOGY CO., LTD., Taoyuan (TW)

(72) Inventor: Chang-Chi Lee, Taoyuan (TW)

(73) Assignee: TAI-SHINY TECHNOLOGY CO., LTD., Taoyuan (TW)

( * ) Notice: Subject to any disclaimer, the term of this patent is extended or adjusted under 35 U.S.C. 154(b) by 75 days.

(21) Appl. No.: 16/591,584

(22) Filed: Oct. 2, 2019

(65) Prior Publication Data

US 2020/0108187 A1    Apr. 9, 2020

(30) Foreign Application Priority Data

Oct. 4, 2018    (TW) .................. 107213475

(51) Int. Cl.
*A61M 1/00* (2006.01)
*A61M 39/24* (2006.01)

(52) U.S. Cl.
CPC ............ *A61M 1/81* (2021.05); *A61M 1/74* (2021.05); *A61M 39/24* (2013.01); *A61M 2205/0216* (2013.01); *A61M 2205/106* (2013.01); *A61M 2210/0618* (2013.01)

(58) Field of Classification Search
CPC .... F04B 33/00; A61M 1/0068; A61M 1/0031; A61M 39/24; A61M 2210/0618; A61M 2205/0216; A61M 1/0023; A61M 2205/073; A61M 1/0005
See application file for complete search history.

(56) References Cited

U.S. PATENT DOCUMENTS

| | | | | |
|---|---|---|---|---|
| 5,902,293 A | * | 5/1999 | Liu | A61H 9/005 |
| | | | | 604/313 |
| 9,234,513 B2 | * | 1/2016 | Cheng | F04B 9/14 |

FOREIGN PATENT DOCUMENTS

| CN | 201175447 Y | * | 1/2009 | ............ A61H 35/04 |
|---|---|---|---|---|
| CN | 103533968 B | * | 8/2016 | ............ A61M 1/804 |
| CN | 103533968 B | | 8/2016 | |
| KR | 20130002266 U | * | 4/2013 | |
| KR | 20130092787 A | * | 8/2013 | ............ A61M 1/00 |
| KR | 20130092787 A | | 8/2013 | |
| TW | 306864 U | * | 9/2006 | ............ A61M 1/00 |

(Continued)

OTHER PUBLICATIONS

Written Opinion of Chinese Patent Office (Year: 2021).*
(Continued)

*Primary Examiner* — Susan S Su
*Assistant Examiner* — Eric Rassavong
(74) *Attorney, Agent, or Firm* — Chun-Ming Shih; HDLS IPR Services

(57) ABSTRACT

A snivel suction apparatus includes a suction mechanism and an air extraction mechanism. The air extraction mechanism is connected to the suction mechanism. The air extraction mechanism includes a pump, a piston, a communicating tube, a first check valve and a second check valve. The piston is arranged on the pump. One side of the communicating tube is connected to the pump. The other side of the communicating tube is connected to the suction mechanism. The first check valve is arranged in the pump and at one side of the communicating tube. The second check valve is arranged on the pump.

10 Claims, 6 Drawing Sheets

(56) References Cited

FOREIGN PATENT DOCUMENTS

| TW | M306864 U | 3/2007 |
|----|-----------|--------|
| TW | M561533 U | 6/2018 |
| TW | M574495 U | 2/2019 |

OTHER PUBLICATIONS

Ground for patent invalidation dated Feb. 26, 2020 of the corresponding Taiwan utility model publication No. M574495.
Ground for patent invalidation dated Apr. 13, 2020 of the corresponding Taiwan utility model publication No. M574495.

* cited by examiner

SNIVEL SUCTION APPARATUS

BACKGROUND OF THE INVENTION

Field of the Invention

The present invention relates to a snivel suction apparatus, and especially relates to a snivel suction apparatus that has a simple mechanism, works without electricity, is easy to operate and improves the safety of use.

Description of the Related Art

Refer to a related art electric snivel suction machine, which is usually compose of an electric pump, a battery, a power switch, an operational button, a collection cup and a silicone suction nozzle. When the related art electric snivel suction machine is used, the silicone suction nozzle is arranged/placed at the nostril. Then the power switch is turned on, so that the battery supplies the required power to the electric pump, and then the electric pump is turned on by pressing the operational button, so that the electric pump generates vacuum pressure, and the silicone suction nozzle sucks the nasal mucus into the collection cup.

However, the overall mechanism of the related art electric snivel suction machine mentioned above is more complex, and using the battery has the inconvenience and security apprehensions of electricity decline and electrolyte leakage. Moreover, if the suction power is too strong or the silicone suction nozzle adsorbs onto the nasal mucosa in the nasal cavity, the nasal mucosa will be hurt due to the suction power is too strong.

SUMMARY OF THE INVENTION

In view of the regrets/disadvantages of the relate art mentioned above, the applicant then researches and develops a snivel suction apparatus to achieve the object of having a simple mechanism, working without electricity, being easy to operate and improving the safety of use.

In order to achieve the object mentioned above and other objects, the present invention provides a snivel suction apparatus. The snivel suction apparatus comprises a suction mechanism and an air extraction mechanism. The air extraction mechanism is connected to the suction mechanism. The air extraction mechanism comprises a pump, a piston, a communicating tube, a first check valve and a second check valve. The piston is arranged on (namely, connected to) the pump. One side of the communicating tube is connected to the pump. The other side of the communicating tube is connected to the suction mechanism. The first check valve is arranged in the pump and at one side of the communicating tube. The second check valve is arranged on the pump.

Therefore, when the snivel suction apparatus of the present invention is used, the suction mechanism is arranged/placed at a nostril. The piston is driven manually in the pump to proceed a reciprocating motion. With the first check valve and the second check valve, a suction motion and an exhaust motion are generated inside the pump. The suction mechanism generates a suction power to suck a nasal mucus through the communicating tube. The object of having a simple mechanism, working without electricity, being easy to operate and improving the safety of use are achieved.

DETAILED DESCRIPTION OF THE INVENTION

Figure 1:
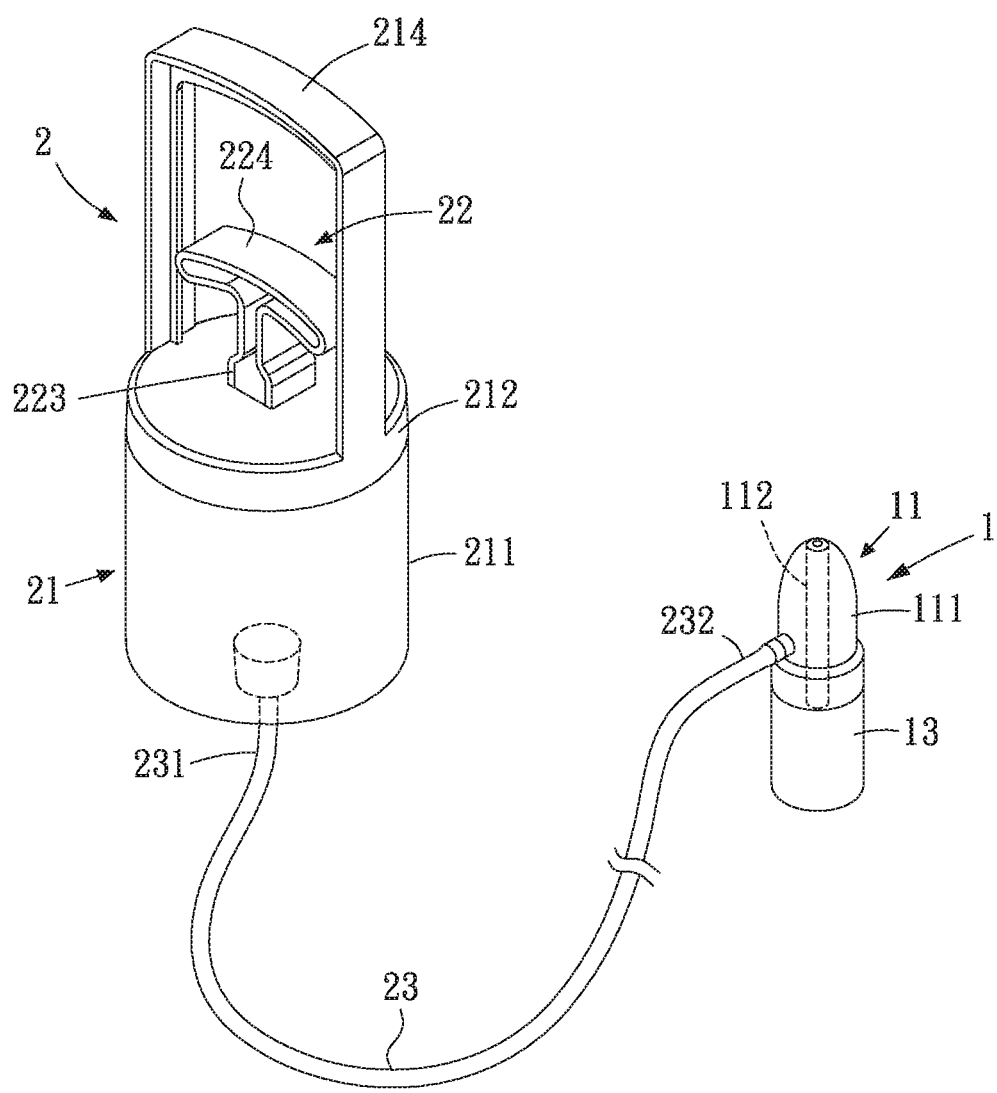
FIG. 1 shows an appearance diagram of the preferred embodiment of the present invention.
Figure 2:
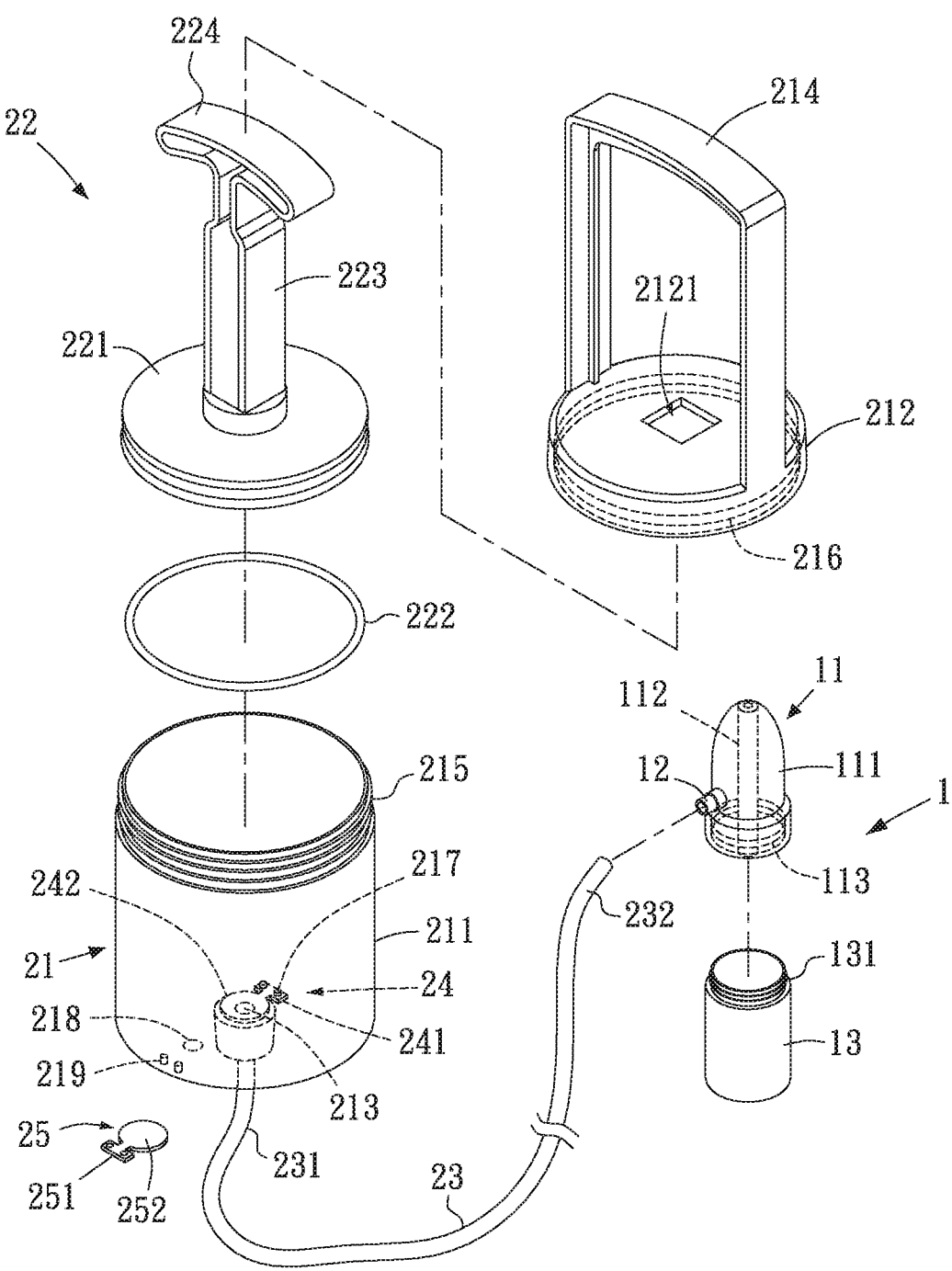
FIG. 2 shows an exploded view of the preferred embodiment of the present invention.

In order to fully understand the objects, features and effects of the present invention, following embodiments and attached figures will describe the present invention in details, as following: Please refer to FIG. 1 to FIG. 4. As shown in FIG. 1 to FIG. 4, the present invention provides a snivel suction apparatus 1000. The snivel suction apparatus 1000 comprises a suction mechanism 1 and an air extraction mechanism 2.

The air extraction mechanism 2 is connected to the suction mechanism 1. The air extraction mechanism 2 comprises a pump 21, a piston 22, a communicating tube 23, a first check valve 24 and a second check valve 25. The piston 22 is arranged on (namely, connected to) the pump 21. One side of the communicating tube 23 is connected to the pump 21. The other side of the communicating tube 23 is connected to the suction mechanism 1. The first check valve 24 is arranged in the pump 21 and at one side of the communicating tube 23. The second check valve 25 is arranged on the pump 21.

Figure 3:
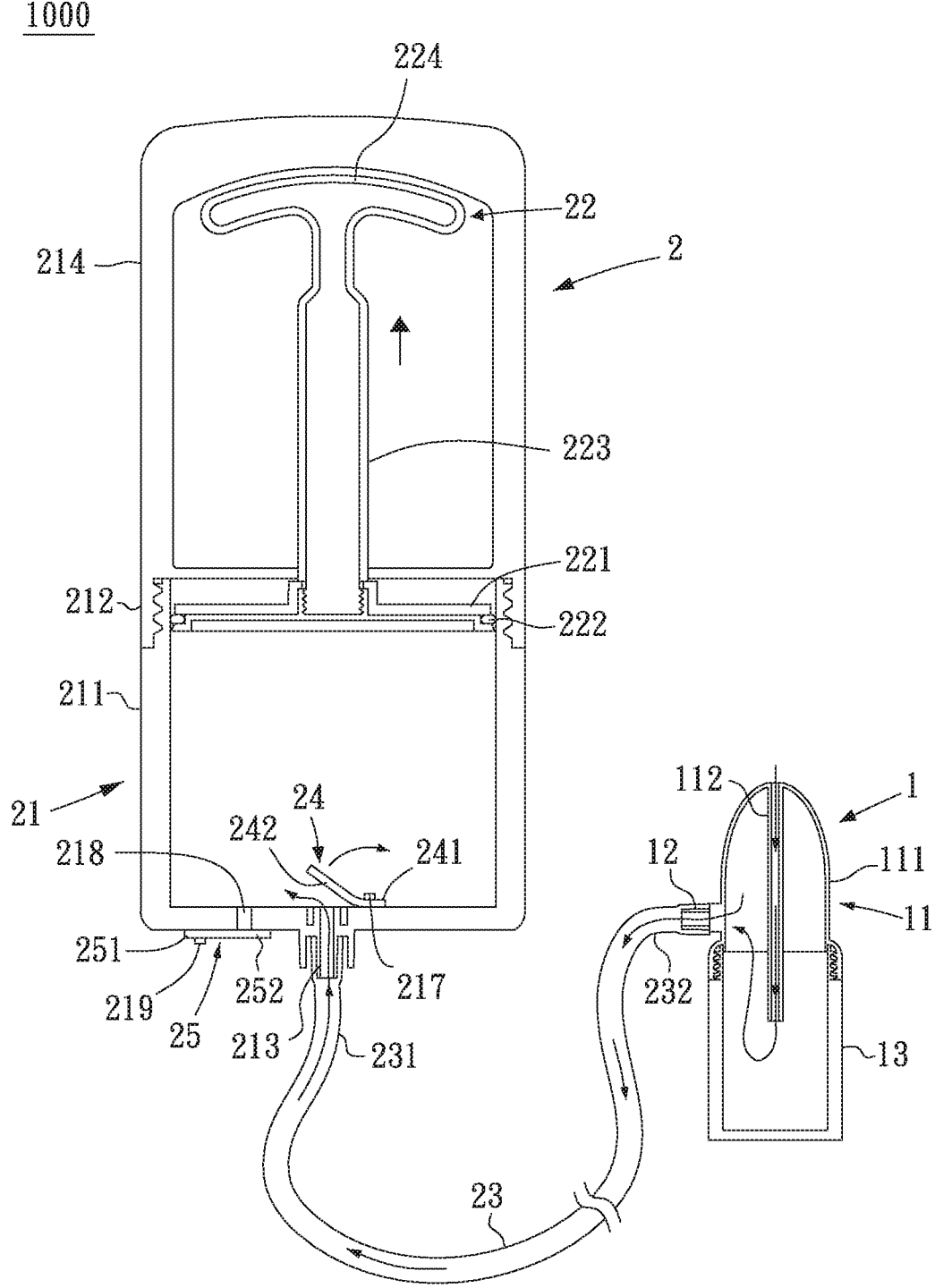
FIG. 3 shows a first sectional view of the usage state of the preferred embodiment of the present invention.
Figure 4:
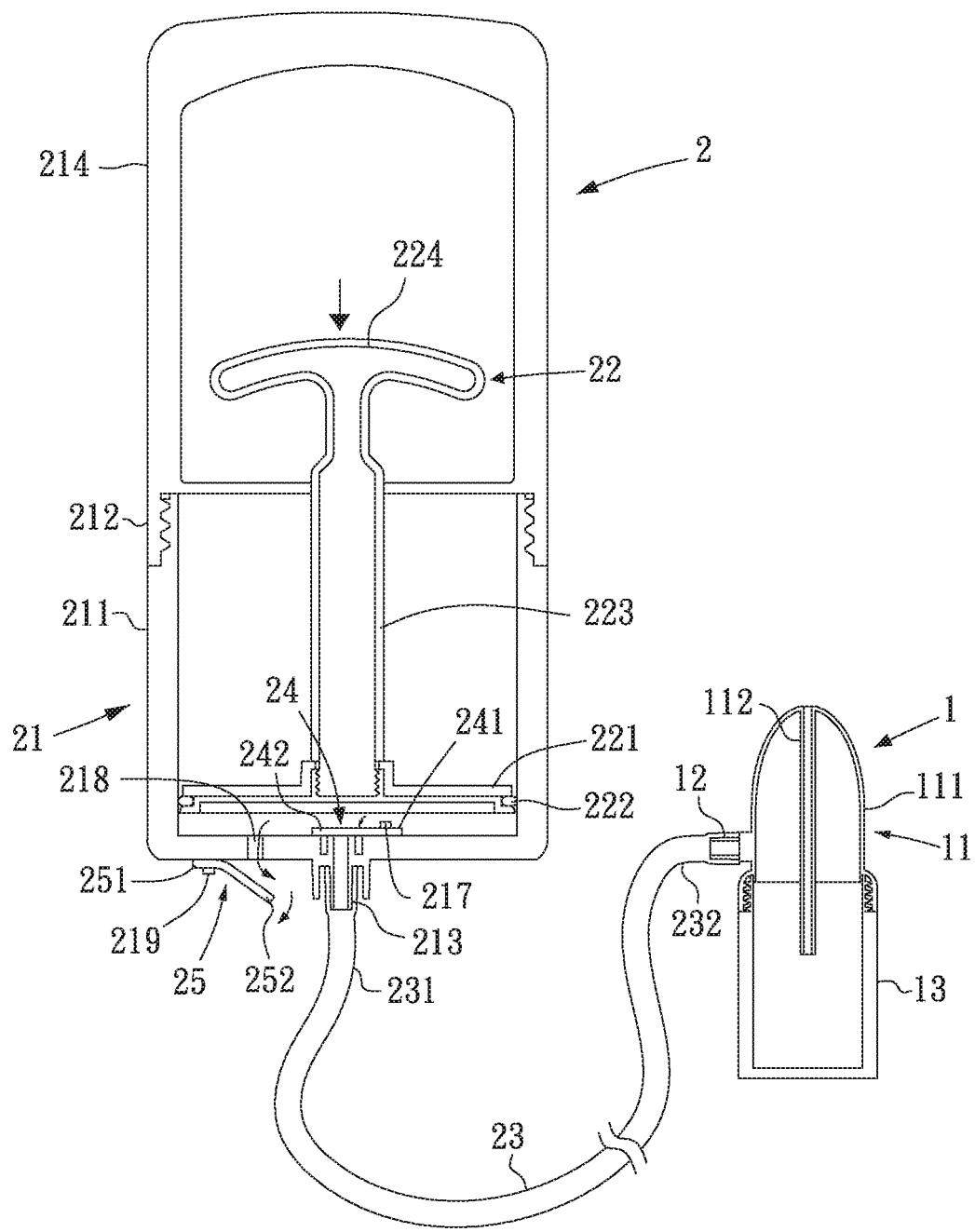
FIG. 4 shows a second sectional view of the usage state of the preferred embodiment of the present invention.

When the snivel suction apparatus 1000 is used, the suction mechanism 1 is arranged/placed at a nostril (not shown in the figures), the piston 22 is driven manually and continuously (or intermittently) in the pump 21 to proceed a reciprocating motion. With the first check valve 24 and the second check valve 25, a suction motion and an exhaust motion are generated inside the pump 21. When the pump 21 performs the suction motion (as shown in FIG. 3), the piston 22 is pulled up, so that the suction mechanism 1 sucks an external air into the pump 21 through the communicating tube 23, and the first check valve 24 pushed by the external air entering the pump 21 is in an on-state (simultaneously, the second check valve 25 is in an off-state), and then a negative pressure (namely, a vacuum pressure) is formed inside the pump 21 to generate the suction motion. When the pump 21 performs the exhaust motion (as shown in FIG. 4), the piston 22 is pushed down, so that the first check valve 24 pushed by an inner air in the pump 21 is in the off-state, so that the inner air in the pump 21 does not exhaust (namely, ceases from exhausting) out of the suction mechanism 1 through the communicating tube 23, and simultaneously the second check valve 25 pushed by the inner air in the pump 21 is in the on-state, and then the exhaust motion is formed inside the pump 21. Therefore, the piston 22 is driven in the pump 21 to proceed the reciprocating motion, and the suction mechanism 1 generates a suction power to suck a nasal mucus through the communicating tube 23. Having a simple mechanism, working without electricity, being easy to operate and improving the safety of use are achieved.

In the preferred embodiment of the present invention, the suction mechanism 1 comprises a suction head 11, a suction manifold 12 and a storage tank 13. The suction manifold 12 is connected to and arranged on the suction head 11. The suction manifold 12 is connected to the other side of the communicating tube 23. The suction head 11 and the storage tank 13 are combined removably. The suction head 11 comprises a housing 111 and a liquid extraction tube 112. The liquid extraction tube 112 is connected to and arranged in the housing 111. The suction manifold 12 is connected to and arranged on one side of the housing 111. The housing 111 and the storage tank 13 respectively comprise bolt connection parts 113, 131 which are mutually moved and butted.

Therefore, the housing 111 of the suction head 11 can be arranged/placed at the nostril, and the liquid extraction tube 112 is toward the nostril. When the piston 22 of the air extraction mechanism 2 is driven in the pump 21 to proceed the reciprocating motion so that the negative pressure is formed inside the pump 21 to generate the suction motion, the suction power is generated through the communicating tube 23 with the suction manifold 12, the liquid extraction tube 112 of the suction head 11 sucks the nasal mucus, and the nasal mucus is drained to the storage tank 13 through the liquid extraction tube 112. When the storage tank 13 would like to be cleaned, the housing 111 of the suction head 11 can be rotated reversely with/from the storage tank 13, so that the housing 111 and the storage tank 13 are mutually detached through the two bolt connection parts 113, 131. After the storage tank 13 is cleaned, the storage tank 13 is combined with the housing 111 through the bolt connection part 131 of the storage tank 13 and the bolt connection part 113 of the housing 111. Therefore, the effect of cleaning easily is achieved.

In the preferred embodiment of the present invention, the pump 21 comprises a tube body 211 and a cover body 212. The cover body 212 is removably combined with one side of the tube body 211. A bottom of the tube body 211 comprises an extension tube 213. One side of the extension tube 213 is connected to one side of the communicating tube 23. The first check valve 24 is arranged inside the tube body 211 and at the other side of the extension tube 213. The second check valve 25 is arranged outside the bottom of the tube body 211. One side of the piston 22 is arranged on (namely, connected to) the tube body 211. The other side of the piston 22 is extended outside the cover body 212. A portable handle 214 is further arranged on a top of the cover body 212. The tube body 211 and the cover body 212 respectively comprise bolt connection parts 215, 216 which are mutually moved and butted. The cover body 212 defines a penetrating hole 2121. The other side of the piston 22 is arranged through the penetrating hole 2121 and extended outside the cover body 212.

Therefore, the piston 22 can be driven in the tube body 211 of the pump 21 to proceed the reciprocating motion, so that the suction motion and the exhaust motion are generated inside the pump 21. When the pump 21 performs the suction motion, the piston 22 is pulled up, so that the suction mechanism 1 sucks the external air into the tube body 211 of the pump 21 through the liquid extraction tube 112, the suction manifold 12, the communicating tube 23 and the extension tube 213, and the first check valve 24 pushed by the external air entering the tube body 211 through the extension tube 213 is in the on-state (simultaneously, the second check valve 25 is in the off-state), and then the negative pressure is formed inside the tube body 211 of the pump 21 to generate the suction motion, so that the suction mechanism 1 generates the suction power to suck the nasal mucus. When the pump 21 performs the exhaust motion, the piston 22 is pushed down, so that the first check valve 24 pushed by the inner air in the tube body 211 is in the off-state, and simultaneously the second check valve 25 pushed by the inner air in the tube body 211 is in the on-state, and then the exhaust motion is formed inside the tube body 211 of the pump 21.

Moreover, the effect of carrying easily or moving easily can be achieved with the portable handle 214. When the pump 21 would like to be cleaned, the tube body 211 can be rotated reversely with/from the cover body 212 (or the portable handle 214), so that the tube body 211 and the cover body 212 are mutually detached through the two bolt connection parts 215, 216. After the pump 21 is cleaned, the cover body 212 is combined with the tube body 211 through the bolt connection part 216 of the cover body 212 and the bolt connection part 215 of the tube body 211. Therefore, the effect of cleaning easily is achieved.

In the preferred embodiment of the present invention, the first check valve 24 comprises a first fixed part 241 and a first valve plate 242. The first valve plate 242 is arranged at one side of the first fixed part 241. A first assembly part 217 is arranged at a position near the extension tube 213 inside the tube body 211. The first fixed part 241 is combined with the first assembly part 217. The first valve plate 242 is arranged at/on the other side of the extension tube 213. Moreover, the second check valve 25 comprises a second fixed part 251 and a second valve plate 252. The second valve plate 252 is arranged at one side of the second fixed part 251. The bottom of the tube body 211 defines a via hole 218. A second assembly part 219 is arranged at a position near the via hole 218 outside the bottom of the tube body 211. The second fixed part 251 is combined with the second assembly part 219. The second valve plate 252 is arranged on the via hole 218.

Therefore, the piston 22 can be driven in the pump 21 to proceed the reciprocating motion, so that the suction motion and the exhaust motion are generated inside the tube body 211. When the pump 21 performs the suction motion, the piston 22 is pulled up, so that the suction mechanism 1 sucks the external air into the tube body 211 through the liquid extraction tube 112, the suction manifold 12, the communicating tube 23 and the extension tube 213, and the first valve plate 242 of the first check valve 24 pushed by the external air entering the tube body 211 through the extension tube 213 is in the on-state. Simultaneously, the second valve plate 252 of the second check valve 25 seals the via hole 218 on the bottom of the tube body 211, and then the negative pressure is formed inside the tube body 211 to generate the suction motion, so that the suction mechanism 1 generates the suction power to suck the nasal mucus. When the pump 21 performs the exhaust motion, the piston 22 is pushed down, so that the first valve plate 242 of the first check valve 24 is pushed by the inner air in the tube body 211, so that the first valve plate 242 seals the other side of the extension tube 213, and simultaneously the second valve plate 252 of the second check valve 25 is pushed by the inner air in the tube body 211, so that the second valve plate 252 away/opened from the via hole 218 is in the on-state, and then the exhaust motion is formed inside the tube body 211 of the pump 21.

In the preferred embodiment of the present invention, the piston 22 comprises a piston head 221, a sealing ring 222, a connecting rod 223 and an operational part 224. The sealing ring 222 is arranged on an outer peripheral of the piston head 221. One side of the connecting rod 223 is combined with the piston head 221. The operational part 224 is arranged on the other side of the connecting rod 223. The piston head 221 is arranged inside the tube body 211 of the pump 21, and the sealing ring 222 and an inner peripheral of the tube body 211 form an air proof. The connecting rod 223 is arranged through the penetrating hole 2121 of the cover body 212. The operational part 224 is arranged outside the cover body 212.

Therefore, when the piston 22 is driven in the tube body 211 of the pump 21 to proceed the reciprocating motion, a pulling force or a pushing force manually applies to the operational part 224, so that the operational part 224 renders that the connecting rod 223 drives the piston head 221 to proceed the reciprocating motion in the tube body 211, and with the first check valve 24 and the second check valve 25, the suction motion and the exhaust motion are generated inside the pump 21. The piston head 221 utilizes the sealing ring 222 and the inner peripheral of the tube body 211 to form the air proof, so that the suction motion and the exhaust motion are more stable and accurate, and then the suction mechanism 1 generates the suction power to suck the nasal mucus to achieve the simple mechanism, working without electricity and operating easily.

In the preferred embodiment of the present invention, the communicating tube 23 can be a flexible tube. Therefore, the communicating tube 23 which is the flexible tube can be utilized, so that the suction mechanism 1 can be moved easily to a required location, or when the suction mechanism 1 is stored, the communicating tube 23 can be wound, so that the suction mechanism 1 and the air extraction mechanism 2 are stacked to each other to save the storage space.

Figure 5:
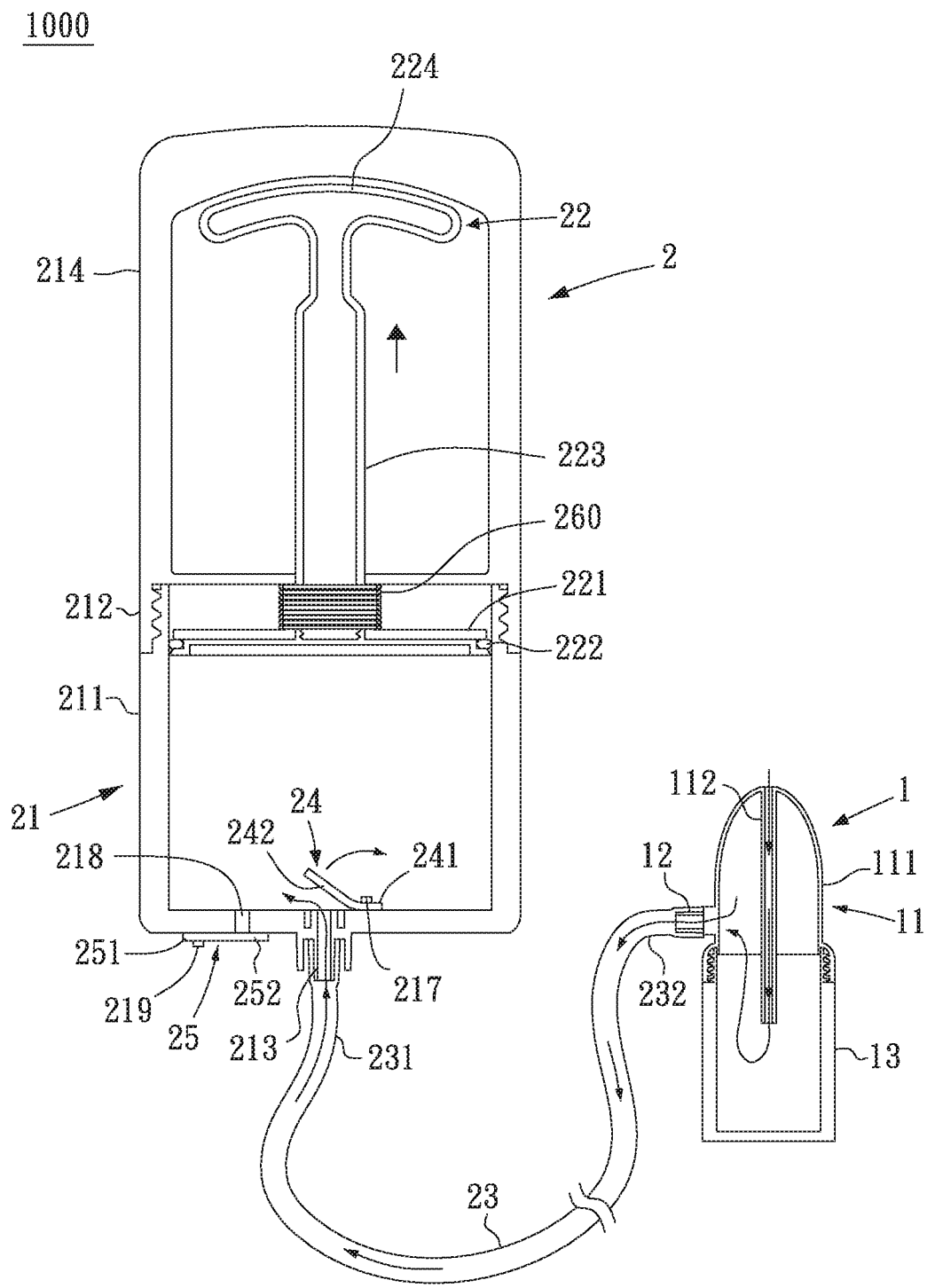
FIG. 5 shows a first sectional view of the usage state of another preferred embodiment of the present invention.
Figure 6:
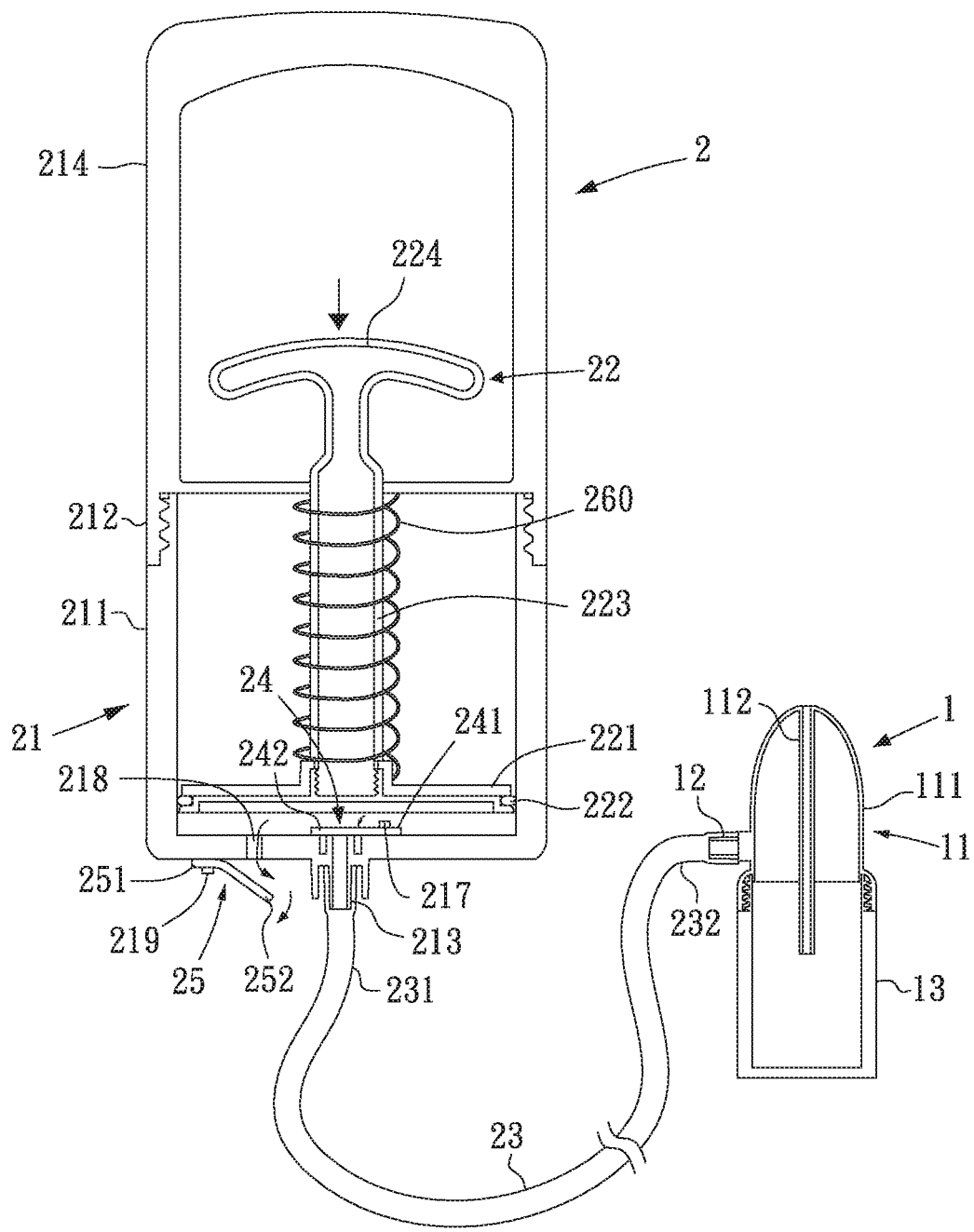
FIG. 6 shows a second sectional view of the usage state of another preferred embodiment of the present invention.

Please refer to FIG. 5 and FIG. 6. As shown in FIG. 5 and FIG. 6, another preferred embodiment of the snivel suction apparatus 1000 of the present invention is shown. The main technical content of this preferred embodiment is basically the same with those of the prior preferred embodiment. However, this preferred embodiment further comprises an elastic member 260. The elastic member 260 is arranged in the pump 21, and is arranged between the cover body 212 and the piston head 221, and the connecting rod 223 is arranged in/through the elastic member 260. Therefore, when the piston 22 is pulled up, simultaneously the piston head 221 applies an external force to the elastic member 260. When the piston 22 loses a pull-up force, according to a reaction force of the elastic member 260, the piston head 221 is driven to push down to push the inner air inside the tube body 211, so that the first valve plate 242 is closed and the second valve plate 252 is opened. Therefore, the required force for operating the piston 22 of the snivel suction apparatus 1000 can be reduced to achieve the object of operating easily.

In the preferred embodiment of the present invention, the elastic member 260 can be a spring.

Although the present invention has been described with reference to the preferred embodiment thereof, it will be understood that the invention is not limited to the details thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A snivel suction apparatus comprising:
    an air extraction mechanism,
    wherein the air extraction mechanism comprises a pump, a piston, a communicating tube, a first check valve and a second check valve; the piston is arranged on the pump; a first side of the communicating tube is connected to a bottom of the pump;
    the first check valve is arranged inside the pump and at the first side of the communicating tube so as to contact and seal the first side of the communicating tube;
    the second check valve is arranged on the bottom of the pump;
        wherein the pump comprises a tube body and a cover body; the cover body is removably combined with a top of the tube body; a bottom of the tube body comprises an extension tube; an outer side of the extension tube is connected to the first side of the communicating tube; the piston is inserted in the tube body so that the piston and the tube body enclose a chamber communicated to an outside environment through the extension tube, a volume of the chamber changes with a motion of the piston, and an end part of the piston is extended outside the cover body; the first check valve communicated to the chamber is arranged inside the bottom of the tube body; the second check valve communicated to the chamber is arranged outside the bottom of the tube body;
    wherein the piston moves toward or away from the bottom to compress or expand the chamber, and the first check valve and the second check valve are arranged at an end of a movable range of the piston:
    wherein when the piston is moved away from the bottom of the tube body to expand the chamber and suck an inlet air into the chamber, the first check valve is turned on by the inlet air airflow pressure and the second check valve is simultaneously turned off by the inlet air vacuum pressure;
    wherein when the piston is moved toward the bottom of the tube body to compress the chamber and exhaust an outlet air from the chamber, the first check valve is turned off by the outlet air pressure and the second check valve is simultaneously turned on by the outlet airflow.

2. The snivel suction apparatus in claim 1, further comprising a suction mechanism, the air extraction mechanism connected to the suction mechanism, a second side of the communicating tube connected to the suction mechanism, wherein the suction mechanism comprises a suction head, a suction manifold and a storage tank; the suction manifold is connected to and arranged on the suction head; the suction manifold is connected to the second side of the communicating tube; the suction head and the storage tank are combined removably.

3. The snivel suction apparatus in claim 2, wherein the suction head comprises a housing and a liquid extraction tube; the liquid extraction tube is connected to inside the housing and is connected to an external environment; the suction manifold is connected to and arranged on one side of the housing; the housing and the storage tank respectively comprise bolt connection parts which are mutually moved and butted.

4. The snivel suction apparatus in claim 1, wherein a portable handle is further arranged on a top of the cover body; the tube body and the cover body respectively comprise bolt connection parts which are mutually moved and butted; the cover body defines a penetrating hole; the end part of the piston is arranged through the penetrating hole and extended outside the cover body.

5. The snivel suction apparatus in claim 1, wherein the first check valve comprises a first fixed part and a first valve plate; the first valve plate is arranged at one side of the first fixed part; a first assembly part is arranged inside the tube body and at the top side of the extension tube; the first fixed part is combined with the first assembly part; the first valve plate is assembled to the top side of the extension tube via the first fixed part.

6. The snivel suction apparatus in claim 1, wherein the second check valve comprises a second fixed part and a second valve plate; the second valve plate is arranged at one side of the second fixed part; the bottom of the tube body defines a via hole; a second assembly part is arranged at a position near the via hole outside the bottom of the tube body; the second fixed part is combined with the second assembly part; the second valve plate is assembled to the tube body via the second fixed part to cover the via hole.

7. The snivel suction apparatus in claim 1, wherein the piston comprises a piston head, a sealing ring, a connecting rod and an operational part;

the sealing ring is arranged to surround the piston head; one side of the connecting rod is combined with the piston head; the operational part is arranged on the other side of the connecting rod; the piston head is arranged inside the pump; the sealing ring and an inner peripheral of the pump form an airproof chamber; the connecting rod is arranged through the pump; the operational part is arranged outside the pump.

8. The snivel suction apparatus in claim 1, wherein the communicating tube is a flexible tube.

9. A snivel suction apparatus comprising:

an air extraction mechanism, wherein the air extraction mechanism comprises a pump, a piston, a communicating tube, a first check valve and a second check valve; the piston is inserted in the pump so that the piston and the tube body enclose a chamber communicated to an outside environment through the extension tube, a volume of the chamber changes with a motion of the piston; a first side of the communicating tube is connected to the pump; the first check valve communicated to the chamber is arranged in the pump and at the first side of the communicating tube; the second check valve communicated to the chamber is arranged on the pump;

wherein the piston moves toward or away from the bottom to compress or expand the chamber, and the first check valve and the second check valve are arranged at an end of a movable range of the piston:

wherein the air extraction mechanism comprises an elastic member arranged in the pump; the piston is arranged through the elastic member;

wherein the first check valve comprises a first valve plate for closing first side of the communicating tube when the first check valve is turned off, and the second check valve comprises a second valve plate for closing the second check valve when the second check valve is turned off;

wherein when the piston is moved away from the bottom of the tube body to expand the chamber and suck an inlet air into the chamber, the first check valve is turned on by the inlet air airflow pressure and the second check valve is simultaneously turned off by the inlet air vacuum pressure;

wherein when the piston is moved toward the bottom of the tube body to compress the chamber and exhaust an outlet air from the chamber, the first valve plate is turned off by the outlet air pressure and the second valve plate is simultaneously turned on by the outlet airflow.

10. The snivel suction apparatus in claim 9, further comprising a suction mechanism, the air extraction mechanism connected to the suction mechanism, a second side of the communicating tube connected to the suction mechanism.

* * * * *